United States Patent [19]

Fitzig et al.

[11] Patent Number: 5,401,496
[45] Date of Patent: Mar. 28, 1995

[54] ORAL ANTI-HALITOSIS PREPARATIONS

[76] Inventors: Simon Fitzig, 122 Casanova St., 14th Floor, 08036 Barcelona; Pablo Wechsler Blecher, 59 Manila St., 12th Floor, 08034 Barcelona; Alejandro Blasco Canfran, 10 Plaza Urquinaona, 08010 Barcelona; Michel Dachs Pujadas, 2 Paseo Manuel Girona, 9th Floor, 08034 Barcelona, all of Spain

[21] Appl. No.: 997,832

[22] Filed: Dec. 29, 1992

[30] Foreign Application Priority Data

Dec. 31, 1991 [ES] Spain .................. 9200137

[51] Int. Cl.6 .................. A61K 7/16; A61K 7/22; A61K 9/68
[52] U.S. Cl. .................. 424/49; 424/48; 424/54
[58] Field of Search .................. 424/49–58

[56] References Cited

U.S. PATENT DOCUMENTS

| | | | |
|---|---|---|---|
| 4,224,307 | 9/1980 | Thiele et al. | 424/49 |
| 4,343,823 | 8/1982 | Todd et al. | 426/250 |
| 4,442,125 | 4/1984 | Thiele | 424/318 |
| 4,525,342 | 6/1985 | Weiss et al. | 424/49 |
| 4,775,694 | 10/1988 | Press et al. | 514/535 |
| 4,797,273 | 1/1989 | Linn et al. | 424/59 |
| 4,966,754 | 10/1990 | Purohit et al. | 424/195.1 |
| 4,971,788 | 11/1990 | Tabibi et al. | 424/49 |
| 5,017,617 | 5/1991 | Kihara et al. | 514/635 |
| 5,059,626 | 10/1991 | Park et al. | 514/658 |
| 5,122,377 | 6/1992 | Miller et al. | 424/439 |
| 5,130,122 | 7/1992 | Tabibi et al. | 424/49 |
| 5,202,146 | 4/1993 | Singer et al. | 426/613 |
| 5,208,028 | 5/1993 | Clements et al. | 424/401 |
| 5,214,035 | 5/1993 | Veatch | 514/179 |
| 5,234,689 | 8/1993 | Lindauer et al. | 424/401 |
| 5,250,289 | 10/1993 | Boothroyd et al. | 424/59 |

FOREIGN PATENT DOCUMENTS 272878  6/1988  European Pat. Off. .

OTHER PUBLICATIONS

Goldberg et al Biofouling 3:193–198 Jul. 15, 1991 "Bacterial Desorption by Commerical Mouthwashes vs. Two–Phase Oil:Water Formulations" (Odex, Agis Ltd, Tel Aviv, Israel comparison with other mouthwashes).

Kobayashi (Sunstar) C.A. 110:44748u (1989) 7 E.P. 272878—29 Jun. 1988.

*Primary Examiner*—Shep K. Rose
*Attorney, Agent, or Firm*—Benjamin J. Barish

[57] ABSTRACT

An oral anti-halitosis preparation adapted to desorb microorganisms and to absorb materials causing halitosis, includes as an active ingredient a synthetic oil, preferably one containing the ester of an alcholol and an aliphatic acid of at least six carbon atoms. Particularly good results were obtained when the synthetic oil is caprylic triglyceride, capric triglyceride, or mixtures thereof.

13 Claims, No Drawings

ORAL ANTI-HALITOSIS PREPARATIONS

FIELD AND BACKGROUND OF THE INVENTION

The present invention relates to preparations of oral (buccal) compositions effective against halitosis.

There exist on the market different mouthwashes (mouth rinses), dentifrices, masticables (chewables) and other dental application products which are palliatives for oral hygiene, acting in different manners.

A. Some prevent dental caries, and are based on fluorinated compounds, such as sodium fluoride, stannous fluoride or sodium monofluorophosphate.

B. Others prevent the formation of bacterial plaque, and are based on antiseptics, such as chlorhexidine, cetylpyridinium chloride, benzalconium chloride, thymol eucalyptol, methyl salicylate, benzoic acid, boric acid, menthol, sanguinarine chloride and others.

C. Others, also preventing bacterial plaque, are based on antibiotics, as for example metronidazole.

An object of the present invention is to provide novel oral preparations for reducing or eliminating halitosis of buccal origin.

BRIEF SUMMARY OF THE INVENTION

According to the present invention, there is provided an oral anti-halitosis preparation adapted to desorb microorganisms and to absorb materials causing halitosis, characterized in that the preparation includes a synthetic oil as an active ingredient.

The novel preparations may be in the form of mouthwashes, dentifrices (creams or gels), masticables (chewables), caramels (candies), etc.

The novel preparations of the present invention act in halitosis reduction or elimination via two different, although simultaneous, processes: (1) by desorption and displacement of bacteria and other types of microorganisms adhering to teeth surface and other sectors of the oral cavity (gums, mucous membrane, tongue, palate, cheeks, etc.), which constitute the so-called baterial plaque; and (2) by absorption and subsequent displacement of the substances segregated by the mentioned microorganisms, which are the immediate originators of oral halitosis. Thus, the synthetic oil acts to separate the mentioned bacterial plaque, by mechanical shear action, during the operations of rinsing (in the case of mouthwashes), toothbrush friction (in the case of pastes, creams or gels), and chewing (in the case of masticables).

According to the preferred embodiments of the invention described below, the active ingredient is a synthetic oil containing the ester of an alcholol and an aliphatic acid of at least six carbon atoms. Particularly good results were produced when the synthetic oil is one selected from the group consisting of caprylic triglyceride, capric triglyceride, and mixtures thereof.

In the case of mouthwashes (liquids), the novel compositions also contain water which forms an apparently homogeneous phase by virtue of the presence of a non-ionic emulsifier, optionally accompanied by 1,2-propylene glycol.

The compositions may also include a quaternary ammonium salt as a co-active principle against the bacterial plaque. The positive ionic charge on the quaternary nitrogen atom attacks the external cell membrane of the bacteria or of the respective microorganisms, which exhibit a superficial negative charge. In the case of mouthwashes, such ammonium salt also acts as a coemulsifier.

The compositions relative to the invention may also contain: one or more flavoring agents; one or more sweeteners; a dyestuff suitable for food use; a fluorinated compound as cariogenic preventive agent; strontium chloride or nitrate, as desensitizer; a bacteriostatic agent; and one or more preservatives.

In the case of dental creams and pastes, the respective composition may also contain ingredients that are conventional for such preparations, as for example: polishing agents (talc, kaolin, alumina, etc.); waxes (beeswax, carnauba wax, etc.); and thickeners (hydroxyethyl cellulose, methylcellulose, carboxy-methyl cellulose, alginates, etc.).

In the case of dental gels, conventional components for this type of preparations may also be included, e.g., humectant (moisturizing) agents (such as glycerol, propylene glycol, etc.); thickeners (such as modified celluloses); and silicas (acting as agents for dispersion or suspension, thickening and/or thixotropy, prevention against coagulation).

In the case of dental pastes, creams and gels, the quaternary ammonium salt may be substituted by lecithin as emulsifier. This component also acts as dispersing, humectant (moisturizing) and anti-oxidation agent.

In the case of masticables (chewables), besides the synthetic oil or oils, there may also be included conventional components for such kinds of products, preferably in their "sugar free" versions, such as: a gum base; polypols with reduced or zero cariogenic index (such as sorbitol) or xylitol, in crystalline or syrup form); stabilizers (such as glycerol or xylitol); and antioxidants for gum base (such as butylhydroxytoluene, BHT, or butylhydroxyanisole, BHA).

In the case of masticables (chewables) the emulsifier would be lecithin, rather than a quaternary ammonium salt.

In order for the oral anti-halitosis preparations to exhibit a good mass (bulk) homogeneity and a good efficacy, the preparation procedure requires the availability, in each case, of the proper agitation-dispersion means, adequate for the characteristics and physical state of the ingredients entering in each composition. In this way, although the compositions include, in a number of occasions, non-miscible substances, such as oils on the one hand and water on the other, or mixtures of insoluble solids with liquids, a perfect homogeneity in all the mass is insured.

The systematic addition of the components forming part of the different preparations is also important. By following a particular order and mode of addition, the physico-chemical operations, imperative for obtaining the desired distribution of the components across the entire mass of the preparation, are facilitated. Thus, it is important in liquid formulations, in which water enters as the base component, that the oil which constitute the active substance should be added gradually and under good agitation to the ionized (or distilled) water, carrying the emulsifier already incorporated. Following, and always preceded by some minimum continued agitation times, sweeteners, flavors, dyestuff, etc., are added.

Following are descriptions, of a non-limitative nature, of some examples of the novel preparations in order to facilitate understanding of the invention.

DESCRIPTION OF SPECIFIC EXAMPLES

Example 1—A Mouthwash

In a stainless steel vessel, provided with an agitator-micronizer or colloidal stirrer-mixer, the following products, that form part of the mouthwash composition, were gradually added:

| | |
|---|---|
| Deionized water | 64.75 parts by weight |
| Synthetic oil (caprylic (60%)/ capric (40%) triglyceride: ESTOL-3604; UNICHEMA) | 32.38 parts by weight |
| Polyoxyethylene-20-sorbitan monolaurate (emulsifier. EMULGIN SML-20; HENKEL) | 2.02 parts by weight |
| Menthol | 0.40 parts by weight |
| Sodium saccharin (sweetener) | 0.08 parts by weight |
| Authorized green dyestuff (VAHINE, of DUCROS. Liquid product, based on CI 19,140 (E-102) abd CI 42,051 (E-131) | 0.37 parts by weight |

The order of addition was the following:

The emulsifier is added to 47 parts of the water, under agitation; the oily material follows, agitation being kept one additional minute once finished the addition and before adding the sweetener, dissolved in the remainder of the water; addition of the menthol follows, fused at 50° to 55° C., if crystalline solid, or as "liquid menthol" (alcoholic syrup, 90 to 91% menthol content), agitation being kept for 30 to 60 seconds after addition is finished; finally, the dyestuff is added, under continued agiation, until total homogeneous aspect.

The preparation obtained exhibited an opalescent aspect, having a pale Nile to pistachio green color.

Example 2—A Mouthwash

Following the same procedure as in Example 1 and in the same assembly, the following composition was prepared:

| | |
|---|---|
| Deionized water | 62.11 parts by weight |
| Synthetic oil (ESTOL-3604) | 31.05 parts by weight |
| Emulsifier (EMULGIN SML-20) | 1.35 parts by weight |
| Hexadecyltrimethylammonium chloride (QUARTAMIN 60-L; KAO) | 0.08 parts by weight |
| MENTHOL | 0.39 parts by weight |
| Xylitol (sweetener) | 4.66 parts by weight |
| Green dyestuff (VAHINE, of DUCROS) | 0.36 parts by weight |

In this case, before the fatty material is added, the emulsifier and the quaternary ammonium salt must be added to the major part of the water, under efficient stirring. A product similar to the one in Example 1 is obtained.

If to the final products obtained in Examples 1 and 2, 10 to 20 parts by weight of iso-propanol or 1,2-propylene glycol (1,2-dihydroxypropane) are added, under agitation during one minute, followed by 24 hours of standing, homogeneous light emerald-green translucent liquid preparations are obtained.

Example 3—A Toothpaste

In a mixing-kneading device, the following components are added:

| | |
|---|---|
| Synthetic oil (Caprylic (50%)/ capric (50%) triglyceride: ESTOL-3605; UNICHEMA) | 64.0 parts by weight |
| Talc | 16.0 parts by weight |
| Kaolin | 8.0 parts by weight |
| Beeswax | 7.0 parts by weight |
| Carnauba wax | 3.0 parts by weight |
| Anise seed oil | 2.0 parts by weight |

The entire mass was kneaded and blended, until a homogeneous mixture was attained, obtaining a product of creamy-pasty and opaque aspect.

Example 4—A Dental Gel

The composition was prepared in the same device as in Example 3, by efficient mixing of the following components:

| | |
|---|---|
| Synthetic oil (ESTOL-3604) | 25.0 parts by weight |
| Refined fish oil (PRIFAT-9811; UNICHEMA) | 5.0 parts by weight |
| Glycerol | 15.0 parts by weight |
| 1,2-Propylene glycol | 7.0 parts by weight |
| Hydrated silica | 15.0 parts by weight |
| Fumed silica | 2.7 parts by weight |
| Bleached lechithin | 4.6 parts by weight |
| Hydroxyethyl cellulose | 1.6 parts by weight |
| Flavor (e. gr., lemon) | 1.0 parts by weight |
| Sodium saccharin | 0.3 parts by weight |
| Sodium monofluorophosphate | 0.8 parts by weight |
| Deionized water | 22.0 parts by weight |

A product of creamy-gelatinous and translucent aspect was obtained.

Example 5—A Masticable (Chewable)

In a mixer-blender, adequate for processing high viscosity pastes, the following composition was prepared.

| | |
|---|---|
| Gum base for masticables (natural rubber, i.e., poly-cis-isoprene, based) | 25.76 parts by water |
| Sorbitol syrup | 38.63 parts by water |
| ESTOL-3604 | 11.59 parts by water |
| PRIFAT-9811 | 11.59 parts by water |
| Glycerol | 2.57 parts by water |
| Xylitol | 3.86 parts by water |
| Flavor (e. gr., peppermint) | 0.97 parts by water |
| Soyabean lecithin | 4.51 parts by water |
| Aspartam (sweetener) | 0.26 parts by water |
| Butylhydroxyanisole (BHA) | 0.26 parts by water |

It is known that halitosis of buccal origin is accompanied by variations of the salivary pH, being lower than 6.5 in cases of puplar gangrene and periodontal affectations and higher than 7.0 in some other pathogenic cases. The salivary pH range of 6.5 to 7.0 may be considered as the normal one.

Thus, it is possible to use salivary pH determination as a symptom and indicator for oral halitosis level.

Each of the preparations of Examples 1 to 5 was tested in 13 selected patients, exhibiting halitosis due exclusively to bacterial plaque. The possibility of other causes of halitosis of systemic origin could therefore be excluded. The buccal pH of all of the patients ranged between 5.8 and 6.5. In a first series of tests, an increase in buccal pH of more than 0.2 units was recorded in all of them, after utilizing:

Mouthwashes: rinsing with 10 ml. during 30 seconds;
Paste or gel: normal oral hygiene (brushing); and
Masticable: 20 minutes of chewing.

The pH evolution was monitored by means of a digital reading pH meter (scale sensitivity: 0.1 pH units), provided with a sound glass electrode of adequate dimensions to fit into the sublingual space.

In five of the mentioned patients, after a self-treatment with the mouthwash of Example 2 during two weeks (three daily rinsings for 30 seconds with 10 ml. of preparate each time), a substantial decrease in halitosis level was confirmed by clinical experience.

Example 6—A Mouthwash

Following the same procedure as in Example 1 and in the same type of equipment, the following composition was prepared:

| | |
|---|---|
| Deionized water | 60.40 parts by weight |
| Synthetic oil: ESTOL 3604, of unichema: caprylic (60%) capric (40%) triglyceride | 26.13 parts by weight |
| Refined col liver oil | 5.00 parts by weight |
| Polyoxyethylene-20-sorbitan monolaureate (emulsifier same as in Examples 6 and 7) | 1.35 parts by weight |
| Chlorhexidine digluconate (20% aqueous solution) | 0.40 parts by weight |
| Menthol | 0.46 parts by weight |
| Xylitol (sweetener) | 6.26 parts by weight |
| Strawberry red food dye, C.I. 14,720, 1% aqueous solution | 0.10 parts by weight |

The order of addition and the procedure were similar to Example 1. The cod liver oil was added just after the synthetic one.

The preparation obtained was similar to the one obtained in Example 1.

The oral preparations described herein have been found to be superior to the oral preparations described in Weiss and Rosenberg U.S. Pat. No. 4,525,342, in which the active ingredient is a vegetable oil or a mineral oil. Thus, the efficacy of mouth bacteria removal using the synthetic oil ESTOL 3604, of unichema: carprylic (60%) capric (40%) triglyceride, was compared to that of soya bean oil, which, in turn, appeared to be the most efficient oily component in a series of mouthwashing systems tested by Weiss and Rosenberg (U.S. Pat. No. 4,525,342).

The tests referred to were performed with four volunteers in a manner similar to the one described by Weiss and Rosenberg in the quoted patent. (See also: M. Rosenberg: *University of Toronto Dental Journal.*, 3/2, 7-11 (1990).

The volunteers swished their mouths for seven consecutive thirty seconds periods. The first four swishes were performed with 7.0 g. of saline. The two subsequent swishing mixtures were composed of 3.5 g. of saline plus 3.5 g. of the respective oil tested. The final (seventh) rinse consisted of 7 g. of saline, again.

Each volunteer performed one such set of seven swishes, two hours after each meal.

Following each swishing, the mixture was expelled from the mouth into 10 ml. graduated centrifuge tubes.

To the expelled saline rinses, 3.5 g. of the respective oil were added, while to the oleo-aqueous ones, 3.5 g. of saline were added.

The resulting mixtures were homogenized by means of a Heidolph Reax 2000 vortex mixer-shaker, set up at maximum power, for 10 seconds. Next, 1 ml. of an aqueous Gentian violet solution of optical density (OD) 1.7 to 1.8 at 585 nm was added to all the tubes. The new resulting mixtures were again mixed by means of the vortex shaker for 10 seconds, at maximum scale. Next, the mixtures were centrifuged at 5,500 revolutions/minute for 25 minutes in a BHG Hermle Z-230 centrifuge.

Thereafter, the exact volume of each phase, in each tube, was recorded, using the tube graduation directly.

Next, 1 to 1.5 ml. portions of the aqueous phase in each tube were extracted by means of a Pasteur pipette and transferred to respective 1.3 ml. small conical tubes, apt for a Sigma-201M centrifuge. The samples were thus centrifuged at 12,000 rev/min in order to perfectly clarify the sample of aqueous phase. This one, once having become totally transparent, was transferred to a 1 ml. cell and the OD of the solution was determined at 585 and at 625 nm means of a Uvikon 810 UV-Vis. spectrophotometer.

In this way, the concentration of dye remaining in the aqueous phase and having not stained microorganisms, could be evaluated.

Table 1 below summarizes the results of the comparative test. Each value represents the amount of Gentian violet remaining in the aqueous phase in each swishing, relative to the first one of each sequence of swishings.

Thus, each 5th and 6th value of each sequence reflects the relative efficacy of each oil-saline system: the lower the value (less remaining one), the more efficient the system for bateria removal.

TABLE 1

Relative Amount of Gentian Violet Remaining in Aqueous Phase

| Volunteer Number | Swish Number | Soya Bean Oil | ESTOL 3604 |
|---|---|---|---|
| 1 | 1 | 1.00 | 1.00 |
|   | 2 | 1.39 | 0.64 |
|   | 3 | 1.31 | 0.54 |
|   | 4 | 1.34 | 0.61 |
|   | 5 | 0.94 Av.: | 0.10 Av.: |
|   | 6 | 0.63 0.79 | 0.61 0.36 |
|   | 7 | 1.27 | 0.98 |
| 2 | 1 | 1.00 | 1.00 |
|   | 2 | 1.40 | 0.72 |
|   | 3 | 0.75 | 0.29 |
|   | 4 | 0.78 | 0.35 |
|   | 5 | 0.87 Av.: | 0.13 Av.: |
|   | 6 | 1.00 0.94 | 0.23 0.18 |
|   | 7 | 1.05 | 0.64 |
| 3 | 1 | 1.00 | 1.00 |
|   | 2 | 2.00 | 0.96 |
|   | 3 | 2.32 | 1.10 |
|   | 4 | 2.21 | 1.02 |
|   | 5 | 0.94 Av.: | 0.53 Av.: |
|   | 6 | 1.87 1.41 | 0.68 0.61 |
|   | 7 | 2.64 | 1.61 |
| 4 | 1 | 1.00 | 1.00 |
|   | 2 | 1.04 | 1.06 |
|   | 3 | 0.88 | 1.16 |
|   | 4 | 0.96 | 1.09 |
|   | 5 | 0.60 Av.: | 0.55 Av.: |
|   | 6 | 0.65 0.63 | 0.66 0.61 |
|   | 7 | 0.88 | 1.40 |

What is claimed is:

1. An oral anti-halitosis mouthwash adapted to desorb microorganisms and to absorb materials causing halitosis, comprising an aqueous phase, an oil phase, a non-ionic emulsifier, and a flavoring agent, characterized in that the oil phase comprises as the active ingredient, a synthetic oil of a caprylic/capric triglyceride mixture, in a concentration effective to mechanically shear, separate, desorb and/or displace oral halitosis originating bacteria and/or bacterial plaque adhering to teeth and to oral cavity gums, mucous, tongue, palate and cheek surfaces.

2. The oral preparation according to claim 1, wherein said synthetic oil is 60% caprylic triglyceride and 40% capric triglyceride.

3. The oral preparation according to claim 1, wherein said synthetic oil is 50% caprylic triglyceride and 50% capric triglyceride.

4. The oral preparation according to claim 1, wherein said active ingredient also includes refined fish oil.

5. The oil preparation according to claim 1, wherein said active ingredient also includes cod liver oil.

6. The oil preparation according to claim 1, further including a quaternary ammonium salt.

7. The oral preparation according to claim 1, further including a lecithin as an emulsifier.

8. In the art of rinsing the mouth with a flavored liquid mouthwash in homogenous emulsion form wherein an aqueous phase, an oil phase, and a non-ionic emulsifier are homogenously admixed, the improvement in halitosis reduction consisting essentially of the step of (A) incorporating in said oil phase, as the essential active anti-halitosis ingredient, a caprylic/capric triglyceride mixture, in a concentration effective to mechanically shear, separate, desorb and/or displace oral halitosis originating bacteria and/or bacterial plaque adhering to teeth and to oral cavity gums, mucous, tongue, palate and cheek surfaces, and (B) rinsing the mouth with said mouthwash after meals at least until the level of the halitosis is decreased.

9. A method of reducing halitosis, comprising: introducing a preparation according to claim 1 into the mouth; swishing said preparation in the mouth for a period of time sufficient to mechanically shear, separate, desorb and/or displace oral halitosis originating bacteria and/or bacterial plaque adhering to teeth and to oral cavity gums, mucous, tongue, palate and cheek surfaces; and expelling said preparation from the mouth.

10. The method according to claim 19, wherein said synthetic oil is a mixture of caprylic triglyceride and capric triglyceride.

11. The method according to claim 9, wherein said synthetic oil is 60% caprylic triglyceride and 40% capric triglyceride.

12. The method according to claim 9, wherein said synthetic oil is 50% caprylic triglyceride and 50% capric triglyceride.

13. The method according to claim 9, wherein the preparation is in the form of a liquid mouthwash and includes a homogenous emulsion of said synthetic oil, water, and an emulsifier.

* * * * *